(12) United States Patent
Urbon et al.

(10) Patent No.: US 8,742,349 B2
(45) Date of Patent: Jun. 3, 2014

(54) PORTABLE RADIOGRAPHIC DETECTOR EXTERIOR BATTERY LATCH AND METHODS FOR USING THE SAME

(75) Inventors: Michael P. Urbon, Churchville, NY (US); Steven D. Daniels, Churchville, NY (US); Robert J. Asento, Rochester, NY (US); Michael P. Simunek, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 109 days.

(21) Appl. No.: 13/620,751

(22) Filed: Sep. 15, 2012

(65) Prior Publication Data

US 2013/0240732 A1    Sep. 19, 2013

Related U.S. Application Data

(60) Provisional application No. 61/537,291, filed on Sep. 21, 2011.

(51) Int. Cl.
*G01J 1/00*    (2006.01)

(52) U.S. Cl.
USPC ........................................ 250/336.1; 379/189

(58) Field of Classification Search
USPC ................................ 250/336.1; 378/189, 190
See application file for complete search history.

(56) References Cited

U.S. PATENT DOCUMENTS

| | | | | |
|---|---|---|---|---|
| 5,660,945 | A  * | 8/1997 | McCormick et al. | 429/123 |
| 5,773,839 | A  * | 6/1998 | Krepel et al. | 250/580 |
| 6,806,681 | B1 * | 10/2004 | Cheiky et al. | 320/107 |
| 7,989,773 | B2 * | 8/2011 | Jadrich et al. | 250/370.09 |
| 2007/0165480 | A1 * | 7/2007 | Wulff | 365/230.06 |
| 2011/0285151 | A1 * | 11/2011 | Sheehan et al. | 292/341.16 |
| 2012/0069966 | A1 * | 3/2012 | Kobayashi | 378/189 |

* cited by examiner

*Primary Examiner* — David Porta
*Assistant Examiner* — Taeho Jo

(57) ABSTRACT

A radiographic imaging detector can include a housing, a radiographic imaging array enclosed by the housing, and a recess to releasably contain a battery in an outer surface of the housing. Certain exemplary embodiments of securing methods and/or battery latch apparatus for the closable recess of the DR detector can include a first catch mechanism configured to be released by force applied in a first direction, a second catch mechanism released by force applied in a second direction different from the first direction, where movement in the first direction can operate to disengage the first catch mechanism from the second catch mechanism, where movement in the second direction can operate to disengage the second catch mechanism for access to the recess, where the second catch mechanism is nearby the first catch mechanism, and where the first and second catch mechanism are actuated using one hand of an operator.

14 Claims, 12 Drawing Sheets

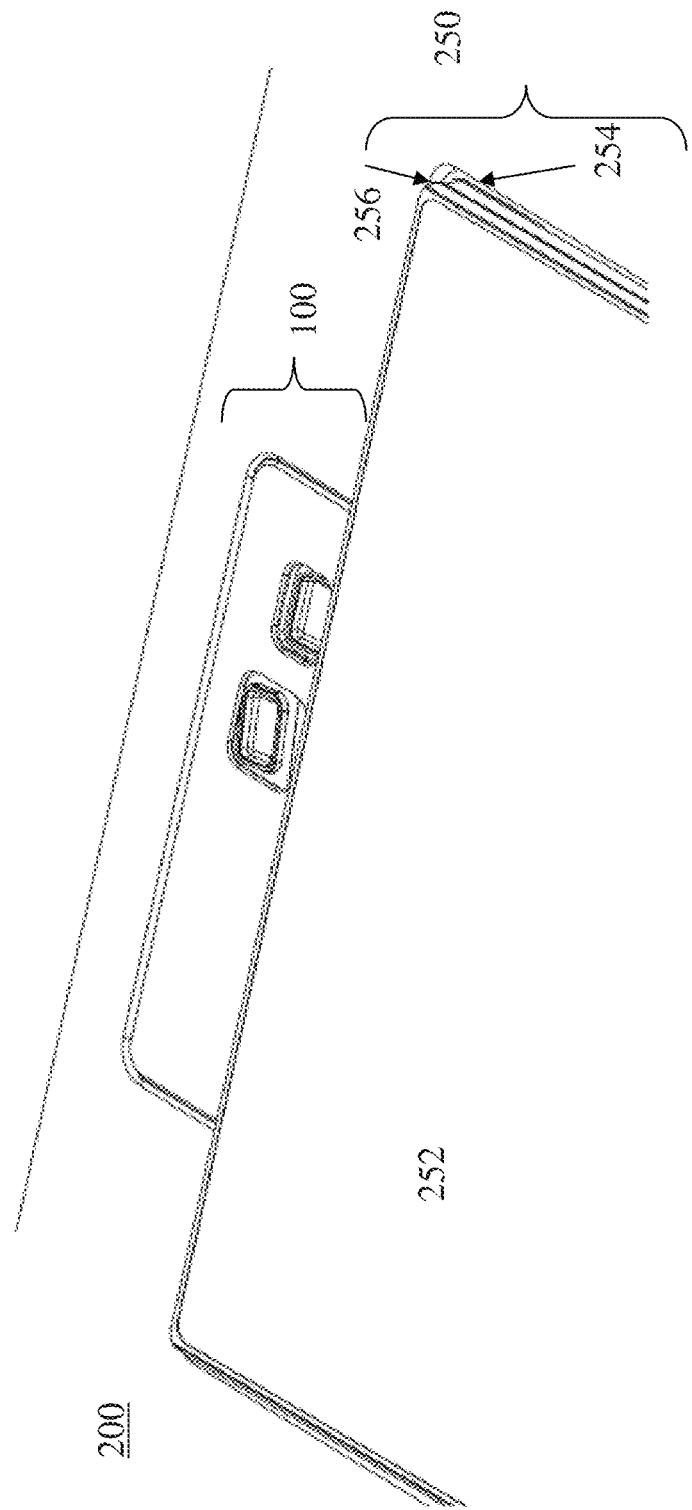
FIG. 2B inserted in detector with battery unlatched

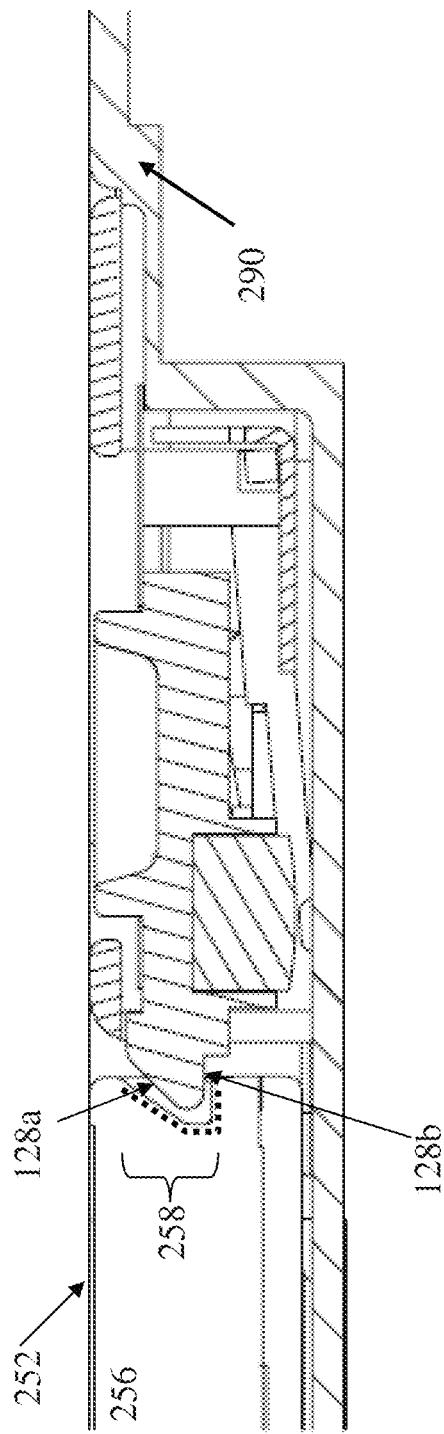
FIG. 2D  inserted in detector with battery cross-sectional view

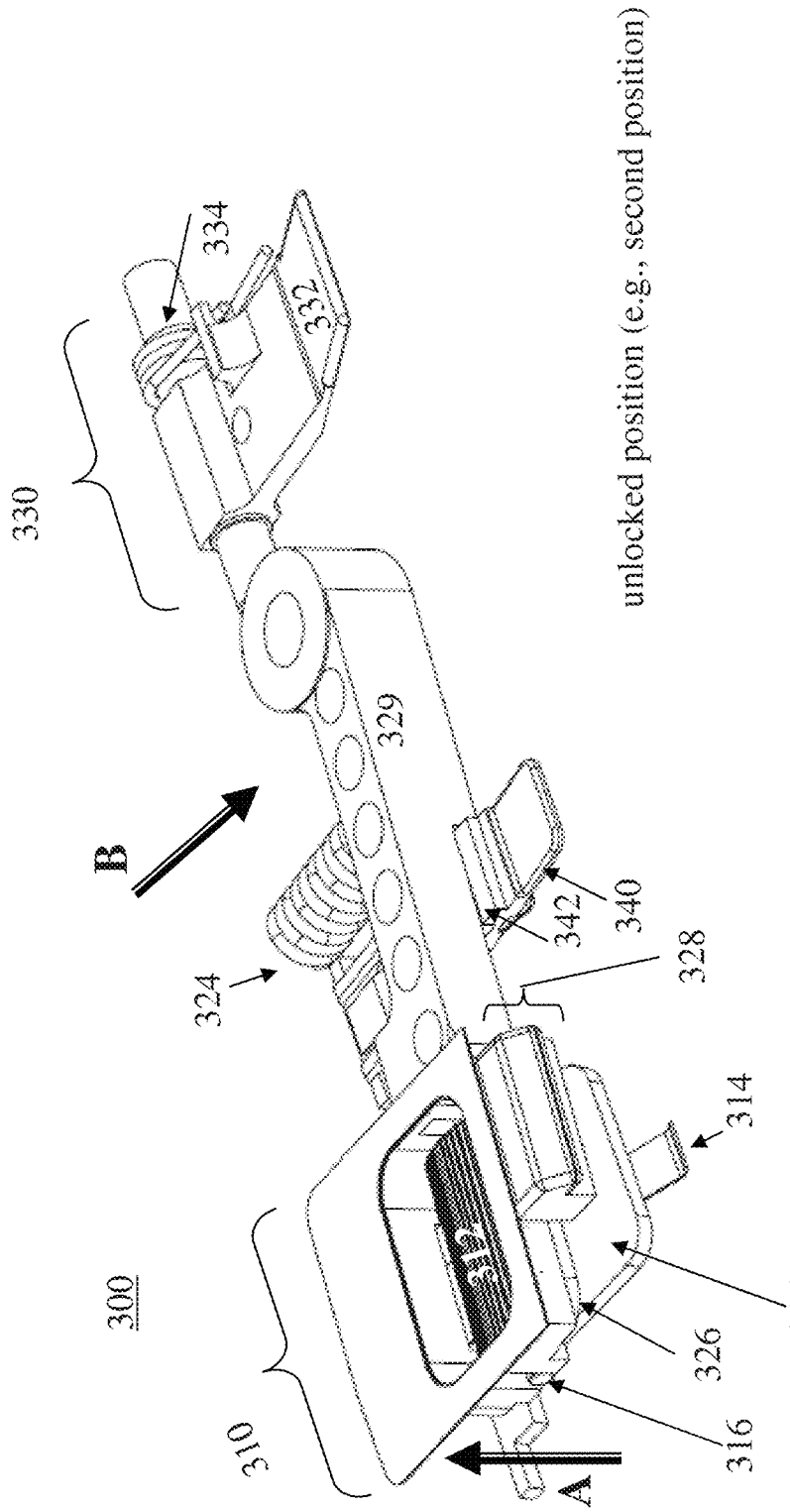

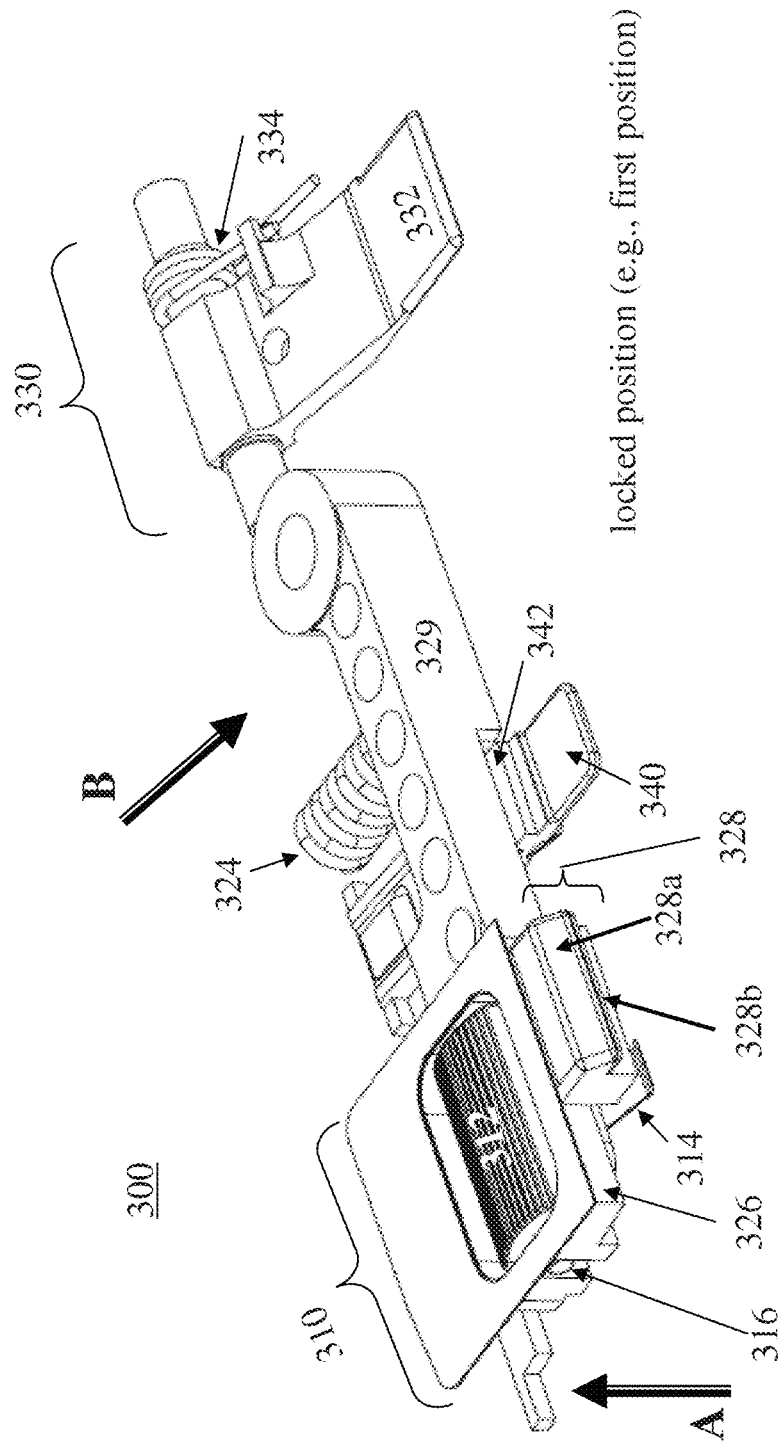

PORTABLE RADIOGRAPHIC DETECTOR EXTERIOR BATTERY LATCH AND METHODS FOR USING THE SAME

CROSS REFERENCE TO RELATED APPLICATIONS

Priority is claimed from commonly assigned, U.S. provisional patent application Ser. No. (a) 61/537,291, filed Sep. 21, 2011, entitled "PORTABLE RADIOGRAPHIC DETECTOR EXTERIOR BATTERY LATCH AND METHODS FOR USING THE SAME", in the name of Steven D. Daniels et al., the disclosure of which is incorporated by reference.

FIELD OF THE INVENTION

The invention relates generally to the field of medical imaging, and in particular to portable radiographic imaging apparatus. More specifically, the invention relates to an external latch (e.g., battery) for a portable radiographic detector for use with a mobile radiography apparatus.

BACKGROUND

There is a need for improvements in digital radiographic (DR) detector design to allow such devices to be more easily transported, deployed and/or operated. In particular, there is a need for a battery latch that can be easily used by the operator (e.g., x-ray technician) and/or also be safe for the patient.

SUMMARY

An aspect of this application is to advance the art of digital radiography.

Another aspect of this application is to address in whole or in part, at least the foregoing and other deficiencies in the related art.

It is another aspect of this application to provide in whole or in part, at least the advantages described herein.

Another aspect of the application is to provide embodiments of external battery latches to allow access to batteries, when used, stored or mounted at a DR detector.

Another aspect of the application is to provide methods and/or apparatus by which radiography detectors can be modified to provide compartments for one or more batteries that can be opened by a single hand of an operator.

Another aspect of the application is to provide methods and/or apparatus by which radiography detectors can be modified to provide battery latches that can be easily used by the operator (e.g., x-ray technician), securely contain a mounted battery, securely close a battery compartment, be positioned in a continuous exterior surface (e.g., liquid/water proof) of a portable radiographic detector, and/or also be safe for the patient.

In accordance with one embodiment, the invention can provide a mobile radiography apparatus that can include radiographic imaging detector, including a housing having upper and lower planar members and side walls; a radiographic imaging array enclosed by the housing; a recess to contain a battery configured to be exposed in an outer surface of the housing; a battery latch module including, a first catch mechanism configured to be released by force applied in a first direction, a first pressure member operatively coupled to the first catch mechanism, a second catch mechanism configured to be released by force applied in a second direction different from the first direction, a second pressure member operatively coupled to the second catch mechanism, where movement in the first direction operates to disengage the first catch mechanism from the second catch mechanism, where movement in the second direction operates to disengage the second catch mechanism to allow the battery to be removed from the recess, where the second catch mechanism is nearby the first catch mechanism, and where the first catch mechanism and the second catch mechanism are actuated by a single hand of an operator.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 2B is a diagram that shows a perspective view of a battery latch unit mounted at a DR detector partially securing a recess in an unlocked position according to one embodiment of the application.

FIG. 2D is a diagram that shows a cross-section view of a battery latch unit mounted at a DR detector in a locked position according to one embodiment of the application.

FIG. 3A is a diagram that shows a perspective view of a battery latch unit in a locked position according to another embodiment of the application.

FIG. 3C is a diagram that shows a perspective view of a battery latch unit in an unlocked position according to another embodiment of the application.

DESCRIPTION OF EXEMPLARY EMBODIMENTS

Figure 1A:
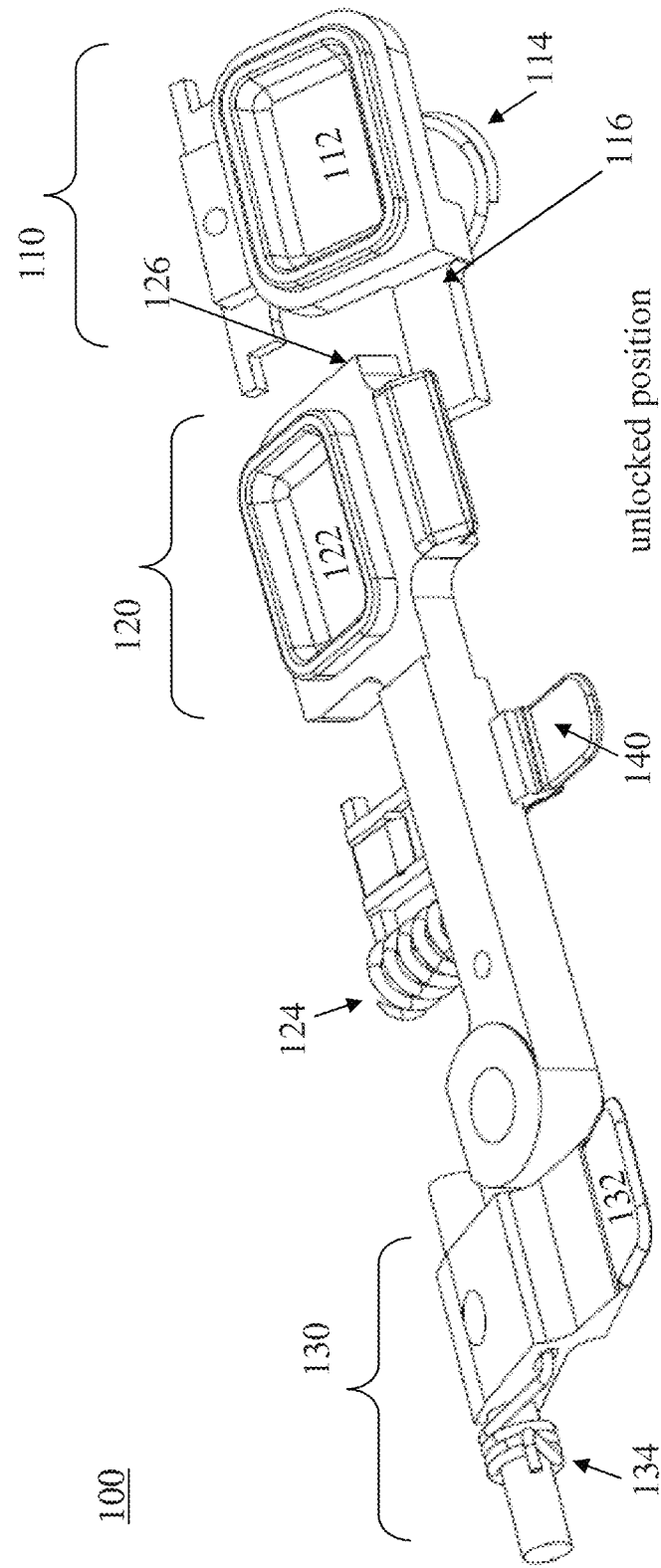
FIG. 1A is a diagram that shows a perspective view of a battery latch unit in an unlocked position according to one embodiment of the application.
Figure 1B:
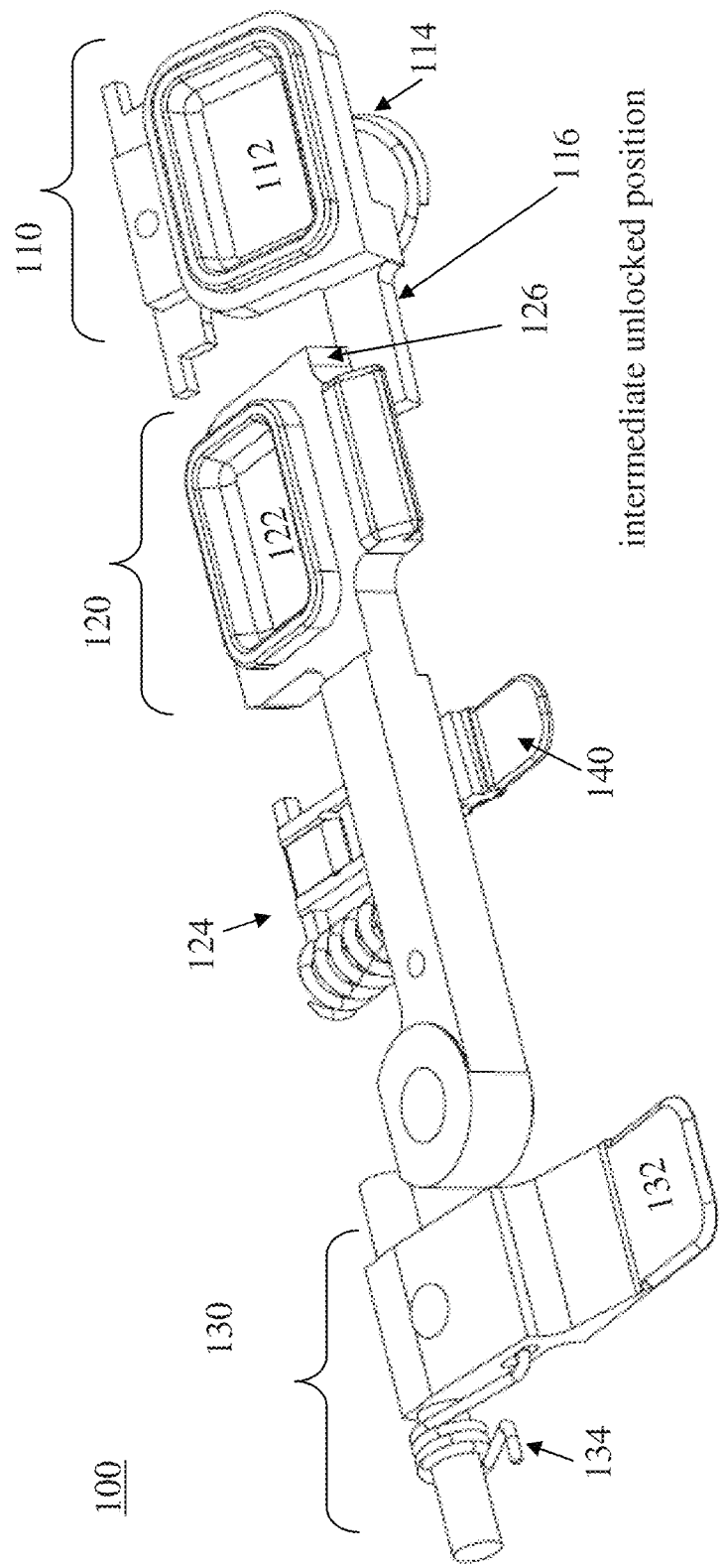
FIG. 1B is a diagram that shows a perspective view of a battery latch unit in an intermediate position according to one embodiment of the application.
Figure 1C:
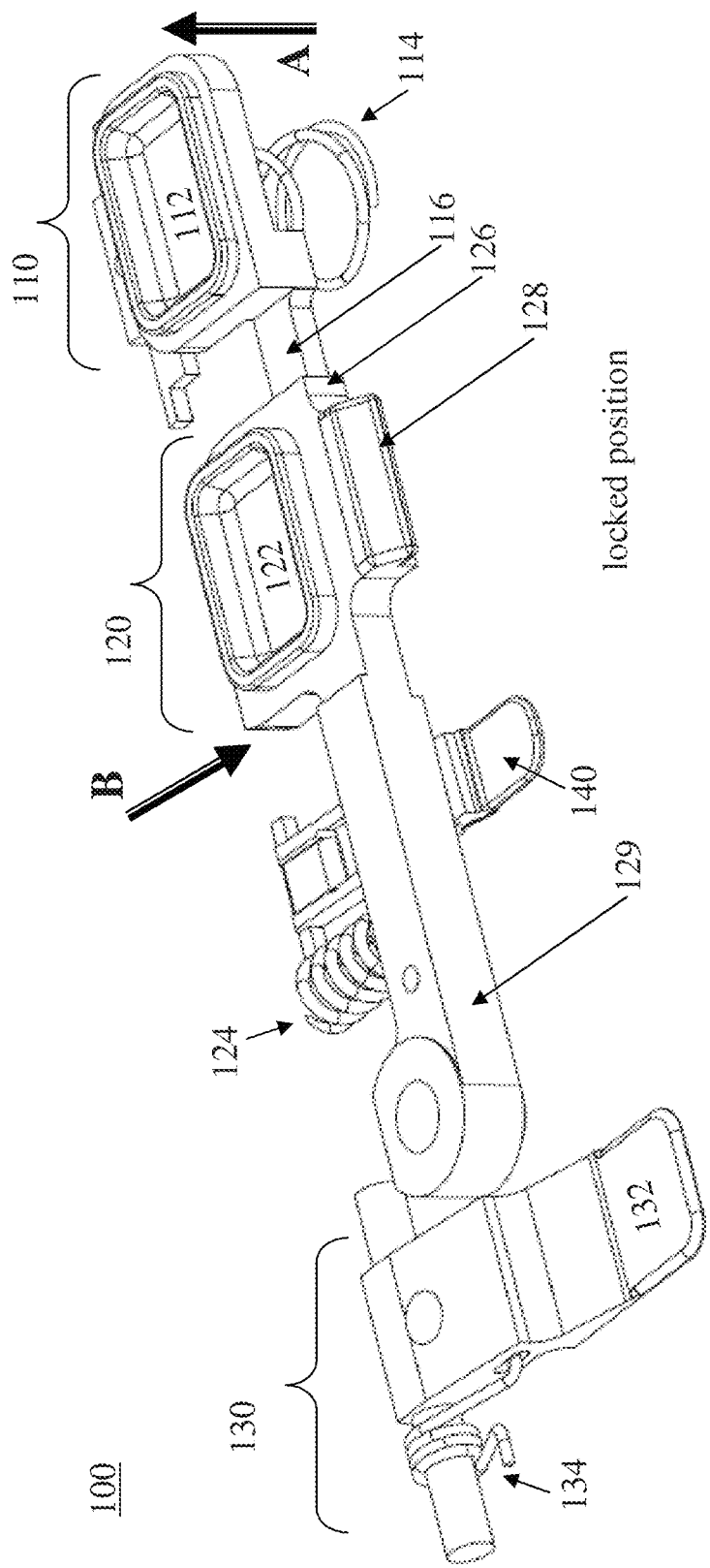
FIG. 1C is a diagram that shows a perspective view of a battery latch unit in a locked position according to one embodiment of the application.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Embodiments according to the application relate to a latch apparatus or battery latch module that can operatively secure or reciprocally lock/unlock a battery compartment for a portable radiographic detector. The detector is a component that can be readily removed and/or moved to different locations preferably for repeated or continuous use or use through a full shift of a radiographic technician.

As described herein, embodiments of an operator (e.g., x-ray technician) actuated battery latch module such as battery latch unit 100, 300 can be operated using a single hand but requires motion in two different directions (e.g., one button with two-directional motion or two buttons with single directional motion) to externally mount an operational battery to a portable radiographic detector (e.g., in a battery compartment exposed at an exterior surface of the detector). In certain exemplary embodiments, the two buttons include single different directional movement. For example, the two different movements or directions can be horizontal and vertical, different directions or orthogonal directions in a single plane or a direction in two orthogonal planes, directions in non-parallel planes, or movement along different directions that are at least 10 degrees apart, at least 20 degrees apart or at least 45 degrees apart. Thus, preferably, no additional or external tool is used to operate the battery latch module to open or to close. The battery latch module does not open using a single directional force (e.g., dropped, or up to 600 Gs).

FIGS. 1A-1D are diagrams that show multiple views of a battery latch unit according to one embodiment for a digital radiographic detector. As shown in FIGS. 1A-1D, an exemplary embodiment of a battery latch unit 100 can include a first actuator 110, a second actuator 120, a release or third actuator 130 to urge the connected battery up or away from the DR detector and a reset or fourth actuator 140 that can operate to reset the battery latch unit 100 from an unlocked position (e.g., second position) to a locked position (e.g., first position). The first actuator 110 and the second actuator 120 can be operated by two digits of a single hand of an operator or x-ray technician. Thus, the first button and the second button are positioned near each other or operatively adjacent (e.g., can be operated by a single human hand) and are accessible or exposed to a surface of the detector. The first actuator 110 and the second actuator 120 shown in FIG. 1A include separate buttons in recessed compartments, however, embodiments herein are not intended to be so limited as any actuators operable by a single hand of the technician can be used. Accordingly, a size and/or shape can vary within dimensions sufficient for use by a human hand. Further, the first actuator 110 and the second actuator 120 can be implemented as projecting or recessed and movable by force generated by a human finger or thumb.

Figure 2A:
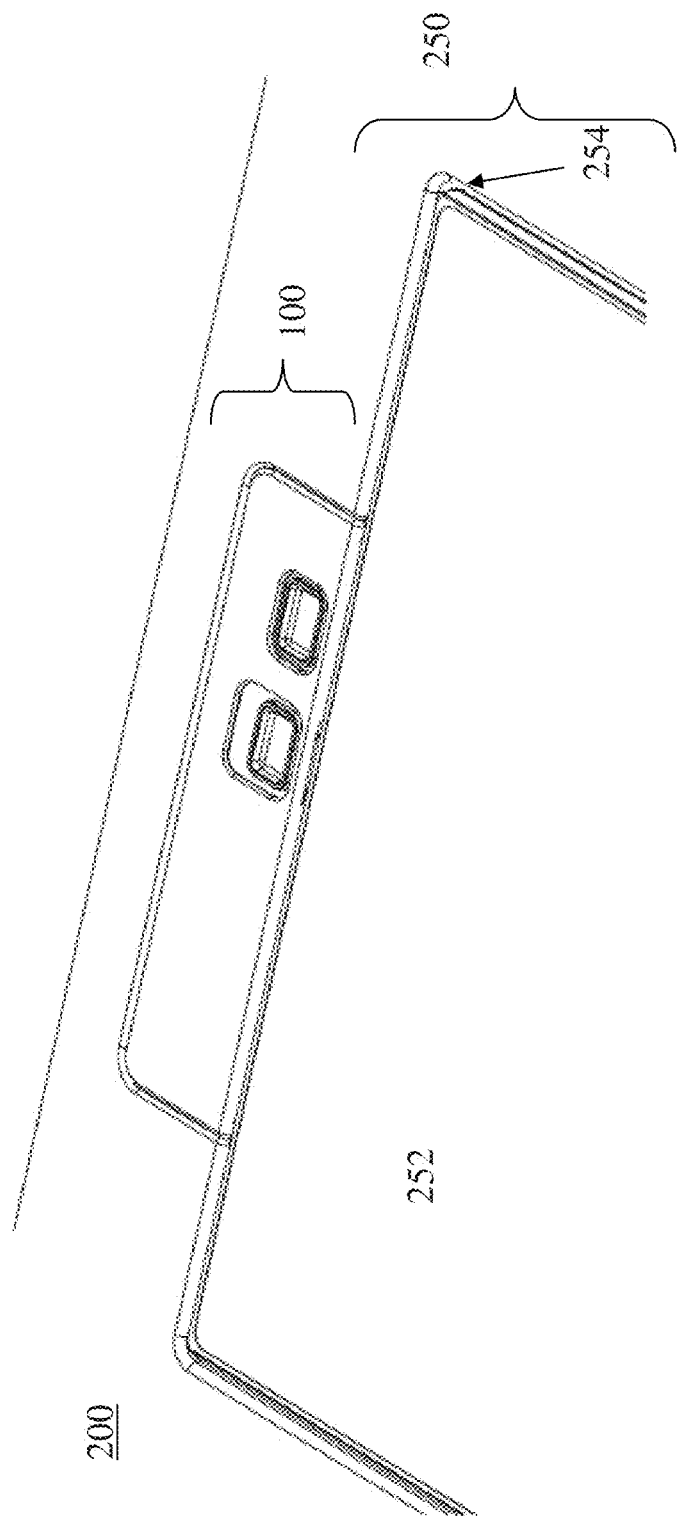
FIG. 2A is a diagram that shows a perspective view of a battery latch unit mounted at a DR detector securing a battery recess in a locked position according to one embodiment of the application.

The battery latch unit 100 can be mounted onto an exterior of the DR detector preferably outside a continuous liquid proof housing or shell. Further, the battery latch unit 100 can be proximate a battery compartment and positioned along at least one single side (as shown in FIG. 2A).

The first actuator 110 can include a first button 112, a first urging member 114 and a first engaging projection 116 and the second actuator 120 can include a second button 122, a second urging member 124, a second engaged unit 126 and a compartment latch 128. The first urging member 114 can force the first button 112 in a direction shown as arrow A in FIG. 1D or away from the detector to be in a first position. In the first position of the first button 112, the first engaging projection 116 can be positioned to resist or prevent movement of the second button 122. For example, in the first position of the first button 112, the first engaging projection 116 can extend into a corresponding recess, slot or hole in the second actuator 120 such as the second engaged unit 126. In the second position of the first button 112, the first engaging projection 116 can be removed from or outside the corresponding second engaged unit 126. In one embodiment, the first engaging projection 116 can not re-enter the corresponding recess, slot or hole in the second actuator 120 when the second actuator 120 (e.g., second button 122) is in the second position.

The second urging member 124 can force the second button 122 in a direction shown as arrow B in FIG. 1D or along a surface of the detector to be in a first position of the second actuator 120. In the first position of the second button 122, the reset actuator 140 can be positioned to not interfere with movement of the second button 122, but in the second position of the second actuator 120 (e.g., unlocked), the reset actuator 140 can be positioned to resist or prevent movement of the second button 122 by the second urging member 124. In one embodiment, the reset actuator 140 has an engaging unit 142 to interlock with the second actuator 120 and resist or prevent the second actuator 120 movement from the second position to the first locked position of the second button 122. In one embodiment, the engaging unit 142 is configured to engage a surface of the second button 122. As shown in FIGS. 1A-1D, the engaging unit 142 can be configured to strike a side surface of a connecting portion 129 that can connect the second button 122 to a pivot point.

In one embodiment, a third urging member 134 can force the release actuator 130 in an opening direction (e.g., along arrow A) of the battery compartment. The release actuator 130 can push against a surface of a battery connected in the battery compartment of the DR detector. Alternatively, the release actuator 130 can push against a surface of the battery compartment or the battery compartment cover.

Certain exemplary embodiments can provide an portion of the battery latch unit 100 to engage a corresponding portion of the battery or battery compartment cover to resist or prevent movement of the mounted battery or the battery compartment in the opening direction (e.g., along arrow A) when the battery latch unit 100 is in the locked or an intermediate position. In one embodiment, the second button 120 can include a compartment catch 128 that can resist or prevent movement of the mounted battery or the battery compartment in the opening direction (e.g., caused by release actuator 130). For example, the compartment catch 128 can have a first guide surface 128a and a second locking surface 128b. In operation, when the compartment cover 252 moves from an open position to a closed position, the reset actuator 140 is released whereby the second button 122 and the first button 112 each can return to the locked position and the catch 128 can enter the corresponding recess 258. Alternatively, the catch 128 can resiliently be pushed slightly backward (e.g., opposite arrow B) by force on guide surface 128a and can slide along a side surface until entering the corresponding recess 258. In the corresponding recess 258, the locking surface 128b can resist or prevent battery 256 movement by the third urging member 134 of the release actuator 130 when the second actuator 120 is in the first position (e.g., FIGS. 1B-1C) and until the second actuator has moved to the second position (e.g., FIG. 1A) or unlocked position. The corresponding recess 258 can include a corresponding the surface 258a so that the recess 258 matches the compartment catch 128. The corresponding recess 258 can be in the battery 256 or the compartment cover 252.

Figure 2C:
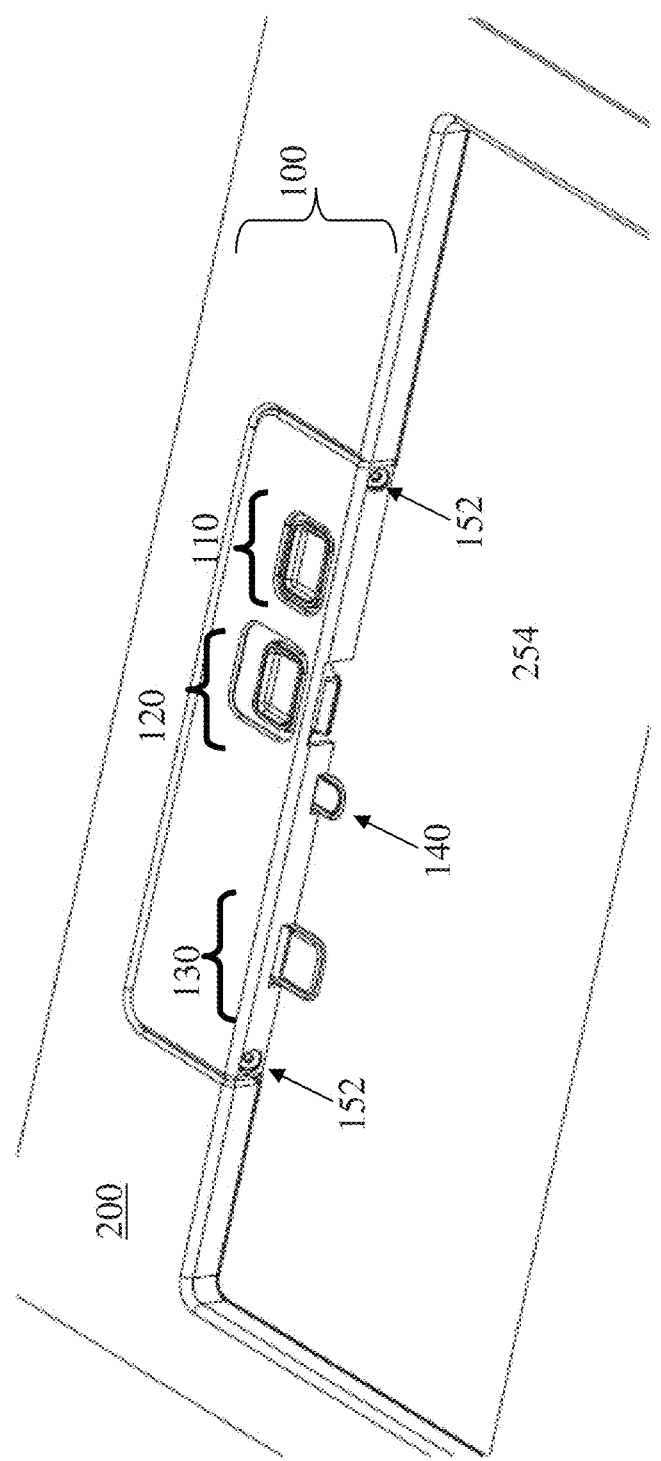
FIG. 2C is a diagram that shows a perspective view of a battery latch unit mounted in a locked position at a DR detector where a cover of the recess is removed according to one embodiment of the application.

FIGS. 2A-2D are diagrams that show views of a battery latch unit embodiment mounted at a DR detector securing a battery compartment according to the application. As shown in FIG. 2C, a single battery locking unit 100 can be mounted outside an exterior shell of a DR detector. Accordingly, battery locking module 100 can provide a leak proof access to a battery compartment 250. As shown in FIG. 2C, the battery locking module 100 can be an integral unit secured by fasteners 152 such as screws or the like to the exterior shell or surface of the DR detector. Fasteners 152 can be permanent, releasable or removable as known to one skilled in the art.

As shown in FIG. 2A, the battery latch unit 100 is in a locked position securing the battery compartment 250 where the according to one embodiment the first actuator 110 is in an upward or first position and the second actuator 120 is in the locked position and can not be moved (e.g. pulled sideways or back). Further, the catch 128 is secured in the recess 258.

As shown in FIG. 2B, the battery latch unit 100 is in an unlocked position whereby a battery is accessible in the unlocked and partially opened battery compartment. In FIG. 2B, the first actuator 110 is moved to a pushed down or unlocked position, which allowed the second actuator 120 to be moved (e.g. pulled backward) to the second or unlocked position. The movement of the second actuator 120 to the second position released the catch 128 from the recess 258. Further, the movement of the second actuator 120 to the second position allowed the third urging member 134 to move the release actuator 130 against a portion of the battery compartment to push the battery compartment cover 252 to the partially opened position shown in FIG. 2B. Thus, in one embodiment, the width of the opening of the battery compartment cover shown in FIG. 2B can be directly or indirectly related to the mechanical linkage or size of the third urging member 134 and the release actuator 130. As shown in FIG. 2B, a battery 256 can be mounted in the partially opened battery compartment.

FIG. 2C shows the battery locking unit 100 in the locked position with the battery compartment cover (e.g., and battery) removed. Thus, the release actuator 130 is in an extended position (e.g., spaced away from a bottom surface of the compartment or DR detector 200 surface). In FIG. 2C, the reset actuator 140 is in an unlocked position (e.g., moved toward the bottom surface of the compartment or DR detector 200 surface). The reset actuator 140 allowed the first actuator 110 to move back to its first locked position and the second actuator 120 to move to its first locked position.

FIG. 2D is a cross-section of the battery latch unit 100 mounted at an exterior surface of the DR detector taken through the second button 112. As shown in FIG. 2D, the battery latch unit 100 is shown in a locked or intermediate position where the catch 128 is secured in the recess 258. FIG. 2D also shows the contiguous exterior surface 290 of the DR detector.

Figure 3B:
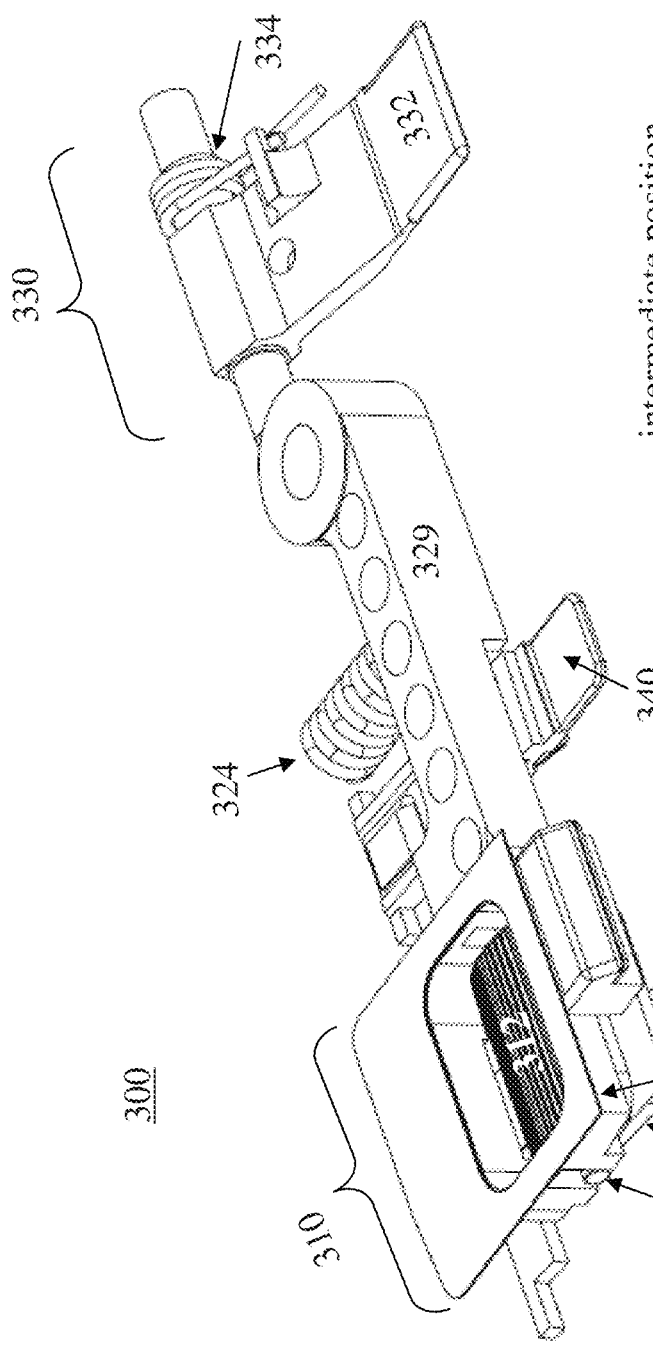
FIG. 3B is a diagram that shows a perspective view of a battery latch unit in an intermediate position according to another embodiment of the application.
Figure 4:
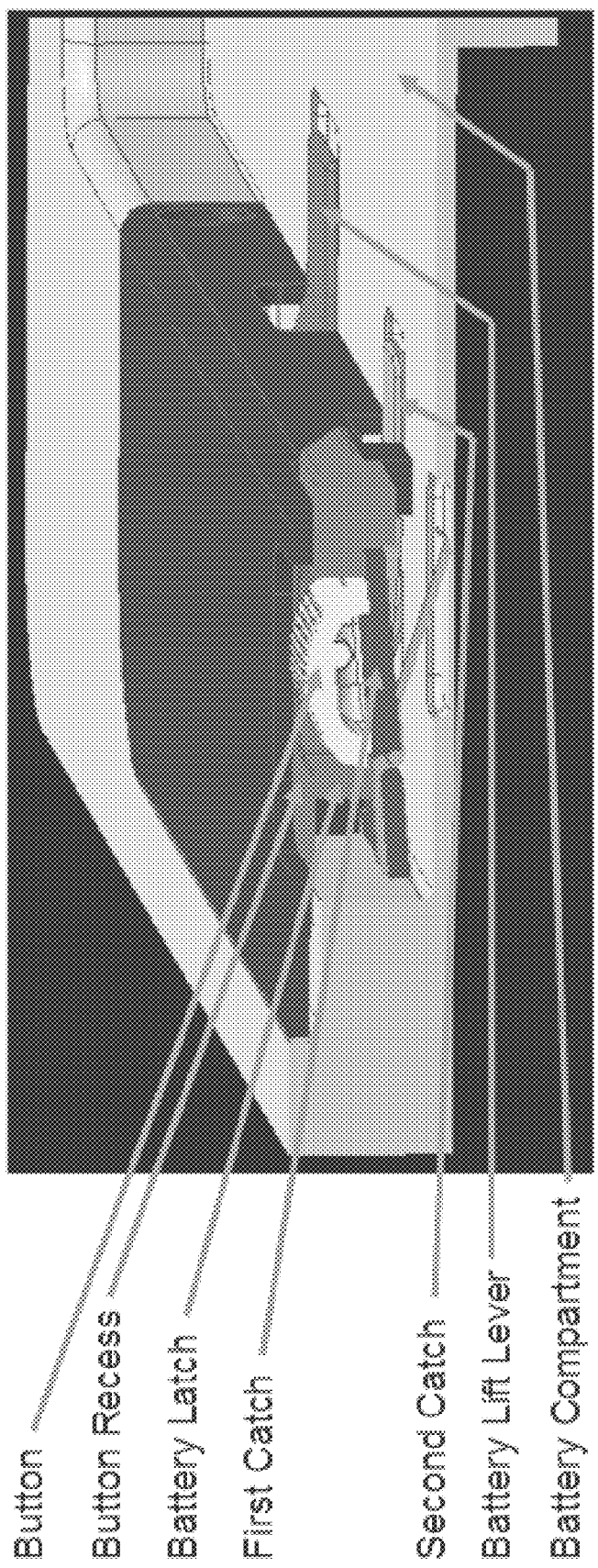
FIG. 4 is a diagram that shows a perspective view of a battery latch unit mounted in a locked position at a DR detector where a cover of the recess is removed according to another embodiment of the application.
Figure 5:
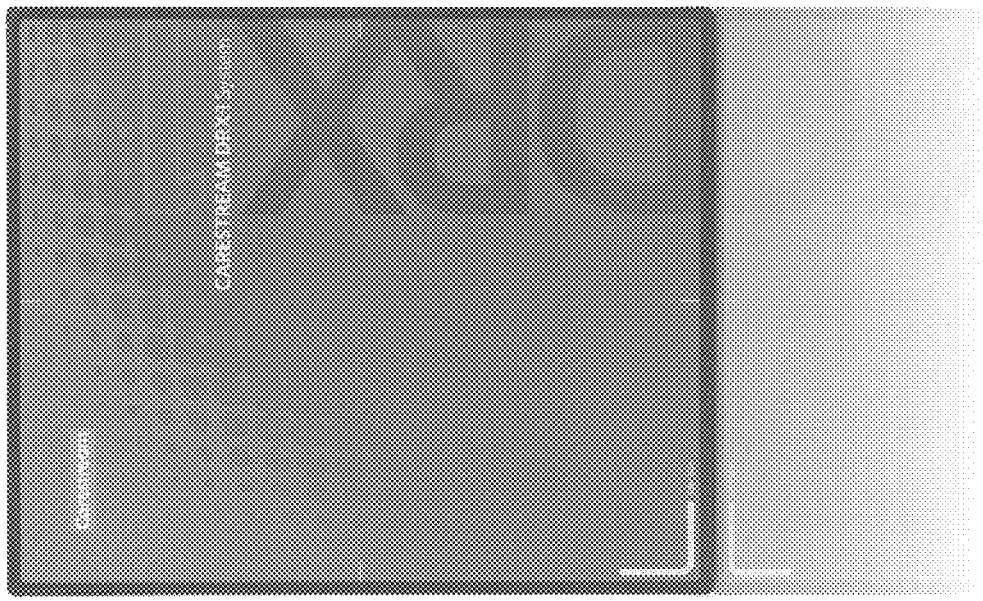
FIG. 5 is a diagram that illustrates a perspective view of an embodiment of a related art DR detector having a storage area for battery.
Figure 5:
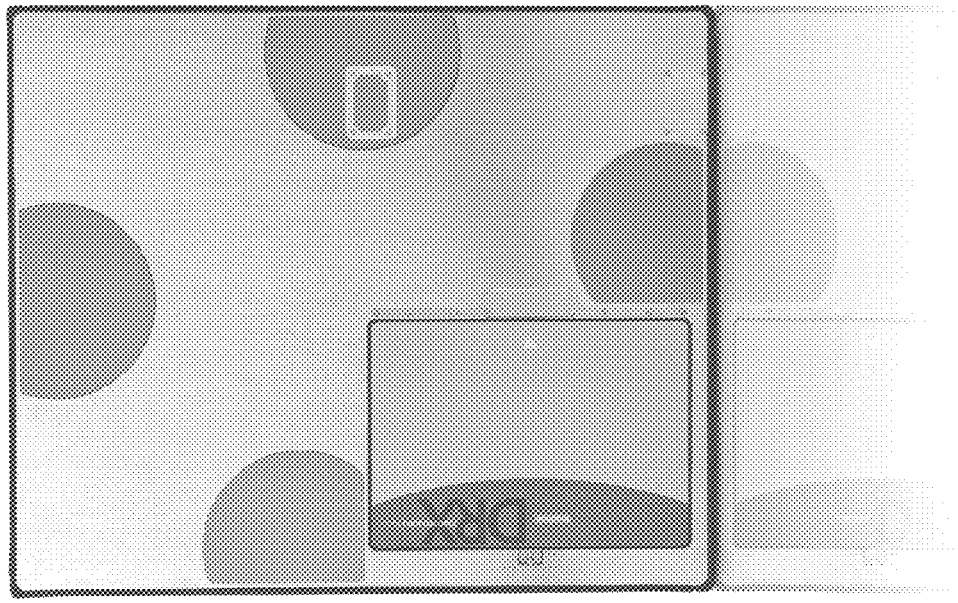

FIGS. 3A-3C are diagrams that show multiple views of a battery latch unit embodiment for a digital radiographic (DR) detector. As shown in FIGS. 3A-3C, an exemplary embodiment of a battery latch unit 300 can include a first actuator 310, a release actuator 330 to urge the connected battery up or away from the DR detector and a reset actuator 340 that can operate to reset the battery latch unit 300 from an unlocked position (e.g., second position, FIG. 3A) to a locked position (e.g., first position, FIG. 3C). The first actuator 310 can be operated by a single digit of a single hand of an operator or x-ray technician. The first actuator 310 is shown in FIG. 3A as a rounded rectangular button in a recessed compartment, however, embodiments herein are not intended to be so limited as any actuators movably operable by a single hand of the technician (e.g., to move in a first unlocking direction that can enable movement in a second different unlocking direction) can be used. Thus, for example, the shape/size of the first actuator 310 can be different (e.g., round, rectangular), unlocking connectors can be different and/or the relative position of the first actuator 310 to the exterior surface can be different (e.g., graspable, a projection, a slidable member, extend above a DR exterior surface, etc.).

The first actuator 310 can include a first button 312, a first urging member 314, an engaging projection 316, a second urging member 324, an engaged unit 326, and a compartment catch 328. The first urging member 314 can force the first button 312 (e.g., and engaging projection 316) in a direction shown as arrow A in FIG. 3C or away from the detector, e.g., to be in its first position. The second urging member 324 can force the first button 312 in a direction shown as arrow B in FIG. 3A or parallel to a surface of the detector toward the intermediate position of the first button 312. In the first position of the first button 312, the first engaging projection 316 can be positioned to resist or prevent movement of the first button 312 in a prescribed or unlocking direction (e.g., opposite arrow B). In the first position of the first button 312, the reset actuator 340 can be positioned to not interfere with movement of the first button 312. However, in the second position of the first actuator 310 (e.g., unlocked), the reset actuator 340 can be positioned to resist or prevent movement of the first button 312 by the second urging member 324 (e.g., released from an unlocked position). In one embodiment, the reset actuator 340 has an engaging unit 342 to interlock with the first actuator 310 and resist or prevent the first actuator 310 movement from the second position to the intermediate position or the first locked position of the first button 312. As shown in FIGS. 3A-3C, the engaging unit 342 can be configured to strike a side surface of a connecting portion 329 that can connect the first button 312 to a pivot point (sliding portion or the like).

As shown in FIGS. 3A-3C, a third urging member 334 can force the release actuator 330 in an opening direction (e.g., along arrow A) of the battery compartment. The release actuator 330 can push against a surface of a battery mounted in the battery compartment 254 of a DR detector. Certain exemplary embodiments can provide an portion of the battery latch unit 300 (e.g., catch 328) to resist or engage a corresponding portion of the battery or compartment cover to resist or prevent movement of the mounted battery in the battery compartment 250 in the opening direction (e.g., along arrow A) when the battery latch unit 300 is in the locked or an intermediate position.

As shown in FIGS. 3A-3C, in one embodiment the first button 310 can include a compartment catch 328 that can have a first guide surface 328a and a second locking surface 328b. In operation, when the first button 312 moves from the intermediate position to the unlocked position, the catch 328 can be removed from a corresponding recess 258 to disengage the second locking surface 328b. When the first button 312 moves from the unlocked position to the intermediate position, the catch 328 can be enter the corresponding recess 258 to engage the second locking surface 328b. The locking surface 328b can resist or prevent battery 256 movement by the third urging member 334 of the release actuator 330 when the first actuator 310 is in the first position or intermediate position (e.g., FIGS. 3B-3C) and until the first actuator 310 has moved to the second position (e.g., FIG. 3A) or unlocked position. The corresponding recess 258 can include a corresponding shape (e.g., surfaces 258a, 258b) so that the recess 258 matches the compartment catch 328. However the shape of the recess 258 and the catch 328 can be changed as known to one skilled in the art. In one embodiment, the corresponding recess 258 can be in the battery 256 or the compartment cover 252.

As shown in FIG. 2A-2C, a single battery locking or latch unit 100 can be positioned along a single short side of the battery compartment. Alternatively, the battery locking module 100 can be positioned along a long side or cross between multiple sides or edges of the battery compartment and be a contiguous integral device, a discontinuous locking device (e.g., two or more sliding members). In one embodiment, a DR detector apparatus can include a battery locking module securing multiple batteries.

When a portable DR detector is dropped, a battery latch module should be secured to reduce or prevent patient exposure to unsafe voltages. A battery latch return spring strong enough to resist an impact load (e.g., about 600 g's) would be too strong for an operator to actuate comfortably. In some X-ray examinations, the patient can hold the DR detector to keep the DR detector in the correct position so there is a risk that the patient could accidentally unlatch the battery, which can then expose the patient to unsafe voltages. An unlatching tool for unlatching a battery latch can negatively affect operator work flow because the operator has to find the unlatching tool. Further, using two hands to disengage a battery latch for a portable DR detector can negatively affect operator work flow and/or cause additional damage to the DR detector (e.g., drops).

In a locked position of at least one battery latch embodiment, a first locking catch can include a portion or projection that can occupy or correspond to a recess or pocket in the second locking catch. First directional movement (e.g., applied by operator movement of a first button) against a first urging member can move the first locking catch from an engaged position with a second locking catch. First directional movement against a first urging member can move the first locking catch to place a battery latch module in an intermediate condition where the second locking catch can be operated (e.g., applied by operator movement of a second button). For example, first directional movement can be different from (e.g., described herein) second directional movement. In the intermediate condition of the battery latch module, electric contacts of the radiographic detector to supply power to the battery are not exposed (e.g., to a patient). With the first locking catch in an unlocked position, second directional movement against a second urging member can move the second locking catch from an engaged position to place the battery latch module in an unlocked condition preferably where the battery is pushed above (e.g., by an urging member, reset actuator or the like) an upper surface of the battery latch, the conformal surface and/or the outer surface of the radiographic detector for easy removal. The first directional movement and/or the second directional movement can be two-dimensional or three-dimensional movement. The first and second buttons can be continuously urged (e.g., springs, elastic members, etc.) toward a locked position. The first and second buttons can reciprocally operate or disengage/engage a holding mechanism (e.g., wall, ledge, bump, projection, catch 128) in a locked position. For example, the holding mechanism can controllably engage a portion of the battery compartment, battery and/or battery compartment cover. In one embodiment, the holding mechanism can be operatively connected to the first button or first actuator 110.

When certain exemplary battery latch module embodiments are unlocked, a battery can move to an accessible position extending at least a portion beyond the exterior surface of the portable DR detector and/or an outer surface of battery latch module. In one embodiment, the battery movement to the accessible position can be operatively responsive (e.g., mechanically or electro-mechanically connected) to movement of the battery latch module to the unlocked position.

In certain exemplary embodiments, force applied in a single direction can move the battery latch module from an unlocked position to a locked position (e.g., ordered sequential movement). Moving the battery into an operational position can move the battery latch module from an unlocked position to a locked position. For example, moving the battery into an operational position can apply force (e.g., by operation of the reset actuator, first urging member, second urging member) to both a first locking catch and a second locking catch to move the battery latch module from an unlocked position to a locked position. Single action of moving the battery to an operational position also can engage the battery latch module (e.g., by ordered sequential operation of holding mechanism, first locking catch, second locking catch).

In certain exemplary embodiments, battery latch modules do not expose battery connectors (not shown) of the portable DR detector unintentionally (e.g., by dropping, patient action). For example, movement in one direction can not open the battery compartment to expose battery connectors. In one embodiment, battery connectors can be leak proof and/or located at a side surface of the battery compartment (e.g., opposite the side surface of the battery latch) where the battery compartment is sized or contains urging members to electrically connect the battery connectors to the battery when the battery compartment is closed.

Battery latch module embodiments can be mounted externally to provide a continuous outer surface of the DR detector (e.g., impervious to liquid). The battery latch module can allow no fasteners to be exposed to an outer surface of the battery latch module, the portable radiographic detector or the battery. In certain exemplary embodiments, battery latch modules can be replaced without accessing interior, electrical components, or imaging components of portable radiographic detector. Further, battery latch module embodiments can be repaired/replaced in the field (e.g., customer site). Battery latch module embodiments can be modular and replaced as a single unit. Exemplary battery latch module embodiments and battery housing are liquid proof and do not allow liquids to access the interior of the portable radiographic detector in the locked, unlocked, assembled or disassembled positions.

In certain exemplary embodiments described herein, battery latch modules for portable radiographic detectors and/or methods for using the same can provide various advantages. For example, to insure the battery is retained (e.g., in a battery compartment) during drop impacts, battery latch embodiments can include a spring-loaded "first catch" that blocks the battery latch from moving from the latched position to the unlatched position responsive to the drop impact, and/or can be strong enough to withstand a 600 g impact. In certain exemplary embodiments, operation of the first catch can use or require a "second catch" (e.g., reset actuator) that can hold the battery latch in the unlatched position so the new battery can be inserted past the battery latch. The second catch can sense (e.g., mechanically linked/operated) when the battery is in its fully seated position and then can allow the battery latch to return to the latched or normal position to retain the battery.

To disengage the first catch in certain exemplary embodiments, the operator can depress a button/actuator located in (e.g., a recess) of the battery latch. For example, while holding down the button the operator then can pull back in a direction perpendicular to the first motion, against the edge of the button recess, to unlatch the battery. When the battery is unlatched, a battery lift lever can lift the battery out of the battery compartment or recess far enough for an operator to grasp the lifted battery. Accidental release of the battery latch can be addressed by exemplary embodiments herein requiring two deliberate motions (e.g., perpendicular to each other) by a single hand of the operator.

As described herein, exemplary battery compartments can include a battery compartment cover. However, exemplary embodiments described herein are not intended to be so limited, for example, a battery itself that is mounted within a battery compartment can provide the (e.g., conformal) battery compartment cover.

Embodiments of a battery compartment for portable detectors can include an alignment or connector system that can automatically mate the battery to the portable DR detector (e.g., internal circuitry thereof (not shown)) to provide DC power to the detector when stored or operatively mounted (e.g., a battery compartment cover reciprocally moves to a closed position) in the battery compartment.

As described herein, various embodiments can use engaging elements and engaged elements (e.g., male and female engaging components), which can be reversed. For example, in one embodiment the projections can extend from surface of the first button to the second button to contact corresponding surfaces, grooves or recesses in the second button. Alternatively, the projections can extend from surface of the second button to the first button to contact corresponding surfaces, grooves or recesses in the first button. Further, mechanical combinations of elements, connections/linkages, urging members or interconnection described herein can be implemented using other connections/linkages, urging members or interconnections including but not limited to electro-mechanical or magnetic. In addition, the battery latch module can be reversed and implemented in a mountable battery to engage an exterior surface of the detector.

Embodiments of a detectors, battery latch modules and battery compartments including the same and methods for using the same can include one or more indicators (e.g., audible or visual) that can alert personnel when the battery is mounted (e.g., reaches a charging position) in the battery compartment.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A radiographic imaging detector, comprising:
   a housing having upper and lower planar members and side walls;
   a radiographic imaging array enclosed by the housing;
   a recess to contain a battery configured to be exposed in an outer surface of the housing;
   a battery latch module comprising,
      a first catch mechanism configured to be released by force applied in a first direction,
      a first pressure member operatively coupled to the first catch mechanism,
      a second catch mechanism configured to be released by force applied in a second direction different from the first direction,
      a second pressure member operatively coupled to the second catch mechanism, where movement in the first direction operates to disengage the first catch mechanism from the second catch mechanism, where movement in the second direction operates to disengage the second catch mechanism to allow the battery to be removed from the recess, where the second catch mechanism is nearby the first catch mechanism, and where the first catch mechanism and the second catch mechanism are actuated by a single hand of an operator, where movement in the second direction operates to disengage the second catch mechanism only when the first catch mechanism is released.

2. The radiographic imaging detector of claim 1, where movement in the second direction operates to disengage the second catch mechanism from the second pressure member to allow the second pressure member to push the battery or a compartment cover away from the detector to provide access to the compartment.

3. The radiographic imaging detector of claim 1, where movement in the first direction and the second direction are each two-dimensional or three-dimensional movement.

4. The radiographic imaging detector of claim 1, where movement of the battery in a third direction into an operational position of the battery operates to sequentially or concurrently re-engage both the first catch mechanism and the second catch mechanism.

5. The radiographic imaging detector of claim 1, further comprising:
   a third pressure member operatively coupled to at least the second catch mechanism; and
   a third catch mechanism configured to be released by force applied in a third direction different from the second direction, where movement in the third direction operates to disengage the third catch mechanism from the second catch mechanism.

6. The radiographic imaging detector of claim 5, where the disengaged third catch mechanism is configured to allow the third pressure member to move the second catch mechanism to a locked position, and
   where the disengaged the third catch mechanism and the second catch mechanism in the locked position are configured to allow the first pressure member to move the first catch mechanism to a locked position.

7. The radiographic imaging detector of claim 1, where the battery latch module is connected to the outer surface of the housing without exposing an interior of the housing, where the outer surface of the housing is a continuous integral surface.

8. The radiographic imaging detector of claim 1, where the battery latch module and battery are mounted to the outer surface of the housing without exposing an interior of the housing, where the outer surface of the housing is a continuous integral surface.

9. The radiographic imaging detector of claim 1, where the second direction is orthogonal to the first direction.

10. The radiographic imaging detector of claim 1, where the first pressure member or the second pressure member is a spring, an elastic member, a mechanical device, a magnetic device or an electromechanical device.

11. The radiographic imaging detector of claim 1, where the first catch mechanism and the second catch mechanism are a mechanical combination of elements.

12. The radiographic imaging detector of claim 1, where the first catch mechanism is recessed in the outer surface and the second catch mechanism is released by movement around a pivot point.

13. The radiographic imaging detector of claim 1, where the first catch mechanism and the second catch mechanism each comprise a movable button.

14. The radiographic imaging detector of claim 1, where a mounted battery in the recess is electrically connected to internal circuitry of the detector.

* * * * *